United States Patent
Prevoir et al.

(10) Patent No.: US 10,835,145 B1
(45) Date of Patent: Nov. 17, 2020

(54) EAR TIPS CAPABLE OF CAPTURING BIOELECTRICAL SIGNALS AND PROVIDING NERVE STIMULATION

(71) Applicant: Bose Corporation, Framingham, MA (US)

(72) Inventors: Shawn Prevoir, Northborough, MA (US); Andrew D. Dominijanni, Waltham, MA (US); Thomas J. Peters, Jr., Sudbury, MA (US); Harsh Anilkant Mankodi, Brighton, MA (US); Yang Liu, Sudbury, MA (US); Corey Ann Le, Tyngsboro, MA (US)

(73) Assignee: Bose Corporation, Framingham, MA (US)

( * ) Notice: Subject to any disclaimer, the term of this patent is extended or adjusted under 35 U.S.C. 154(b) by 0 days.

(21) Appl. No.: 16/448,849

(22) Filed: Jun. 21, 2019

(51) Int. Cl.
*A61B 5/0478* (2006.01)
*A61B 5/00* (2006.01)
*A61B 5/0496* (2006.01)
*A61B 5/0482* (2006.01)
*A61N 1/04* (2006.01)
*A61B 5/0492* (2006.01)

(52) U.S. Cl.
CPC .......... *A61B 5/0478* (2013.01); *A61B 5/0482* (2013.01); *A61B 5/0496* (2013.01); *A61B 5/6817* (2013.01); *A61B 5/0492* (2013.01); *A61B 5/6803* (2013.01); *A61B 2562/0209* (2013.01); *A61N 1/0456* (2013.01)

(58) Field of Classification Search
CPC ............................ A61B 5/0478; A61B 5/6817
See application file for complete search history.

(56) References Cited

U.S. PATENT DOCUMENTS

| | | | |
|---|---|---|---|
| 8,249,287 B2 | 8/2012 | Silvestri et al. | |
| 8,506,469 B2 | 8/2013 | Dietrich | |
| 9,918,650 B2* | 3/2018 | Kilsgaard | A61B 5/0478 |
| 10,057,675 B2 | 8/2018 | Mankodi et al. | |
| 2005/0059870 A1* | 3/2005 | Aceti | A61B 5/6815 600/340 |
| 2011/0007929 A1 | 1/2011 | Rabu et al. | |
| 2017/0087364 A1 | 3/2017 | Cartledge et al. | |
| 2017/0361094 A1 | 12/2017 | Cartledge et al. | |

(Continued)

FOREIGN PATENT DOCUMENTS

WO      WO2018103861      *  6/2018

OTHER PUBLICATIONS

Goverdosky et al., Hearables: Multimodal physiological in-ear sensing, Scientific Reports, vol. 7, Article No. 6948, pp. 1-10, 2017, DOI: 10.1038/s41598-017-06925-2.

(Continued)

*Primary Examiner* — Lee S Cohen
(74) *Attorney, Agent, or Firm* — Bond, Schoeneck & King, PLLC (57) ABSTRACT

An ear tip for an earpiece including a body having first and second ends, an inner wall extending between the first and second ends to define a hollow passage to conduct sound waves, and an outer wall connected to the inner wall of the body at the first end and tapering away from the inner wall toward the second end. The ear tip further includes first and second electrically conductive elements arranged on an outer surface of the deformable outer wall.

13 Claims, 7 Drawing Sheets

(56) References Cited

U.S. PATENT DOCUMENTS

| | | |
|---|---|---|
| 2018/0021564 A1 | 1/2018 | Goodall et al. |
| 2018/0177421 A1* | 6/2018 | Kilsgaard ............ A61B 5/6817 |
| 2018/0235540 A1 | 8/2018 | Kirszenblat et al. |
| 2018/0295439 A1 | 10/2018 | Garrett |

OTHER PUBLICATIONS

Kidmose et al., A Study of Evoked Potentials from Ear-EEG, IEEE Transactions on Biomedical Engineering, vol. 60, No. 10, pp. 2824-2830, Oct. 2013, DOI: 10.1109/TBME.2013.2264956.

Kappel et al., Dry-Contact Electrode Ear-EEG, IEEE Transactions on Biomedical Engineering, vol. 66, No. 1, pp. 150-158, Jan. 2019, DOI: 10.1109/TBME.2018.2835778.

Looney et al., The In-the-Ear Recording Concept: User-Centered and Wearable Brain Monitoring, IEEE Pulse, vol. 3, No. 6, pp. 32-42, Nov. 2012, DOI: 10.1109/MPUL.2012.2216717.

International Search Report and the Written Opinion of the International Searching Authority, International Application No. PCT/US2020/038590, pp. 1-11, dated Sep. 29, 2020.

* cited by examiner

EAR TIPS CAPABLE OF CAPTURING BIOELECTRICAL SIGNALS AND PROVIDING NERVE STIMULATION

BACKGROUND

This disclosure generally relates to configurations for ear tips for use with earpieces.

SUMMARY

This disclosure is directed to an ear tip that enables capturing of bioelectrical signals and/or providing stimulation of nerves through application of electricity.

In one aspect, an ear tip for an earpiece includes a body having first and second ends, an inner wall extending between the first and second ends to define a hollow passage to conduct acoustic energy, and a deformable outer wall connected to the inner wall of the body at the first end and tapering away from the inner wall toward the second end. The ear tip further includes first and second electrically conductive elements arranged on an outer surface of the deformable outer wall.

Implementations may include one or more of the following. The deformable outer wall can form a generally frustoconical shape around the inner wall. The body can be comprised of silicone, polyurethane, polynorbornene, thermoplastic elastomer (TPE), and/or fluoroelastomer. The first and second electrically conductive elements can be comprised of a metal pad, metal button, metal foil, metal-salt hybrid, polymeric composite, intrinsically conductive polymer (ICP), and/or conductive fabric.

The inner wall can include first and second conductive leads configured to electrically connect with the first and second electrically conductive elements when the outer wall is deformed toward the inner wall. The first and second conductive leads can be spring pins or metal-plated pads. The first and second electrically conductive elements can each extend along the outer surface of the outer wall and an inner surface of the inner wall. The ear tip can include first and second electrical circuit elements connected to the first and second electrically conductive elements, with the first and second electrical circuit elements each extending along an inner surface of the outer wall and an outer surface of the inner wall.

In another aspect, an earpiece includes an acoustic driver for transducing received audio signals to acoustic energy. The earpiece also includes a body having first and second ends, an inner wall extending between the first and second ends to define a hollow passage to conduct acoustic energy from the acoustic driver, and a deformable outer wall connected to the inner wall of the body at the first end and tapering away from the inner wall toward the second end. The earpiece further includes first and second electrically conductive elements arranged on an outer surface of the deformable outer wall.

Implementations may include one or more of the following. The deformable outer wall can form a generally frustoconical shape around the inner wall. The body can be comprised of silicone, polyurethane, polynorbornene, thermoplastic elastomer (TPE), and/or fluoroelastomer. The first and second electrically conductive elements can be comprised of a metal pad, metal button, metal foil, metal-salt hybrid, polymeric composite, intrinsically conductive polymer (ICP), and/or conductive fabric.

The inner wall can include first and second conductive leads configured to electrically connect with the first and second electrically conductive elements when the outer wall is deformed toward the inner wall. The first and second conductive leads can be spring pins or metal-plated pads. The first and second electrically conductive elements can each extend along the outer surface of the outer wall and an inner surface of the inner wall. The earpiece can include first and second electrical circuit elements connected to the first and second electrically conductive elements, with the first and second electrical circuit elements each extending along an inner surface of the outer wall and an outer surface of the inner wall. The earpiece can also include a retention structure having an electrically conductive element.

In a further aspect, a method of fabricating an ear tip configured to detect one or more health parameters includes the steps of: providing an ear tip, wherein the ear tip comprises a body having first and second ends, an inner wall extending between the first and second ends to define a hollow passage, and a deformable outer wall connected to the inner wall of the body at the first end and tapering away from the inner wall toward the second end; and forming first and second electrically conductive elements on an outer surface of the deformable outer wall.

Implementations may include one or more of the following. The method can further include the step of forming first and second conductive leads on an outer surface of the inner wall to electrically connect with the first and second electrically conductive elements when the outer wall is deformed toward the inner wall. The method can also include the step of forming the first and second electrically conductive elements along the outer surface of the outer wall and extending along an inner surface of the inner wall. The method can include the step of forming first and second electrical circuit elements connected to the first and second electrically conductive elements, wherein the first and second electrical circuit elements each extend along an inner surface of the outer wall and an outer surface of the inner wall.

In some implementations, the step forming of the first and second electrically conductive elements can include: aligning a conductive material with the ear tip; and heating the ear tip above a vulcanization temperature of a material forming the ear tip to bond the conductive material to a first portion of the ear tip.

Other features and advantages will be apparent from the description and the claims.

BRIEF DESCRIPTION OF THE DRAWINGS

In the drawings, like reference characters generally refer to the same parts throughout the different views. Also, the drawings are not necessarily to scale, emphasis instead generally being placed upon illustrating the principles of the various examples.

DETAILED DESCRIPTION

This disclosure is directed to configurations of an ear tip that can detect bioelectrical signals, for example, electroencephalogram (EEG) signals, and other health parameters, and/or deliver an electrical signal to the ear, for example, for nerve stimulation. Typical EEG devices are comprised of a series of electrodes attached to a skull cap. However, these devices are uncomfortable, bulky, inconvenient, and not suitable for daily-life situations. The present disclosure relates to an ear tip capable of measuring bioelectrical signals such as EEG signals from the brain and/or providing nerve stimulation. The ear tip includes a body having first and second ends, an inner wall extending between the first and second ends to define a hollow passage to conduct sound waves, and an outer wall connected to the inner wall of the body at the first end and tapering away from the inner wall toward the second end. The ear tip further includes first and second electrically conductive elements arranged on an outer surface of the deformable outer wall.

The examples and implementations disclosed or otherwise envisioned herein can be utilized with any suitable earpiece. Examples of suitable earpieces include Bose® Sleepbuds™ (manufactured by Bose Corporation of Framingham, Mass.), ear tips, earbuds, in-ear headphones, over-the-ear headphones, noise-blocking earplugs, and hearing aids. However, the disclosure is not limited to these devices, and thus the disclosure and embodiments disclosed herein can encompass any earpiece configured to be placed at least partially within human ears.

Figure 1:
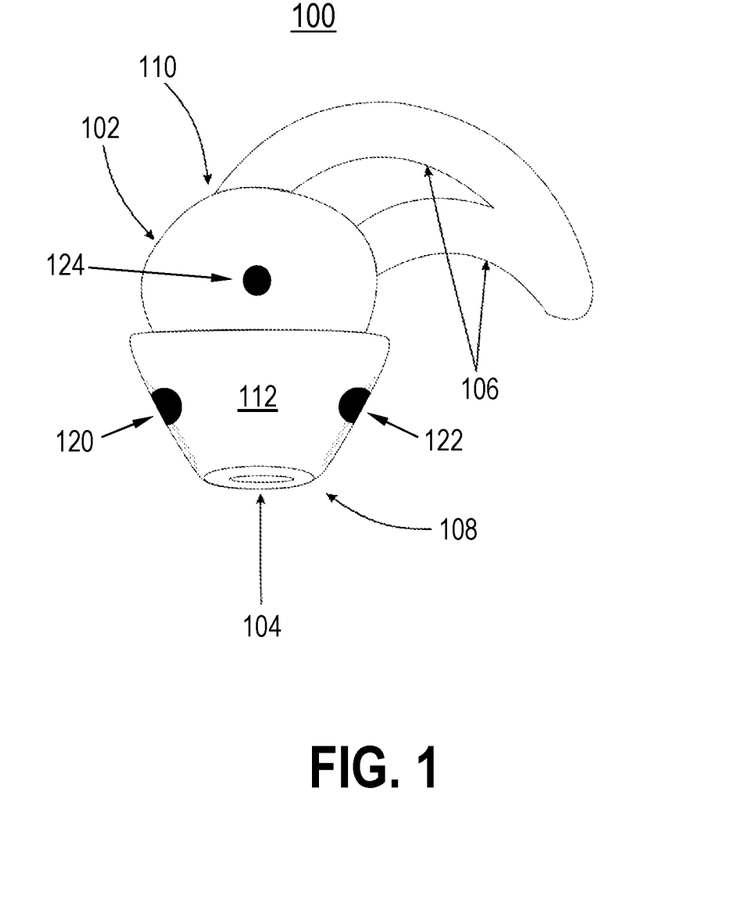
FIG. 1 is an example earpiece.
Figure 2:
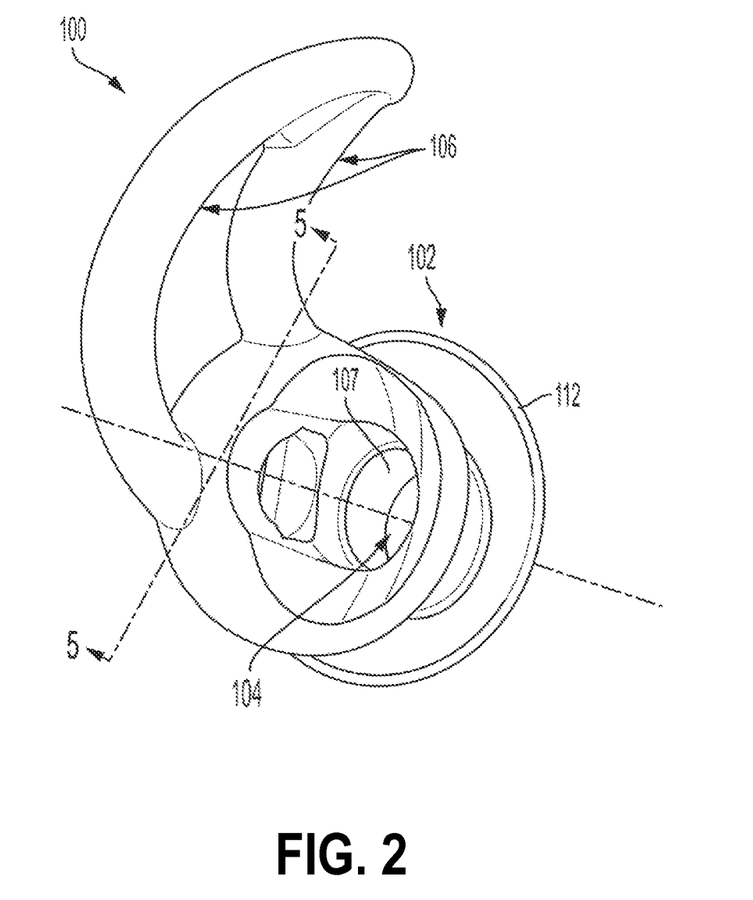
FIG. 2 is a partial cross-sectional view of an example earpiece.

Turning now to the figures, FIG. 1 shows an example earpiece 100 including an ear tip that is configured to fit at least partially into a person's ear canal and a retaining structure configured to hold the ear tip in place when worn. FIG. 2 is a partial cross-sectional view of earpiece 100. The following should be viewed in light of FIGS. 1-2. Earpiece 100 can include body 102, and hollow passage 104, and retaining legs 106. Although FIGS. 1-2 show retaining legs 106 as one embodiment of a retaining structure, this disclosure is not limited to such a configuration. Any type of retaining structure is contemplated. Alternatively, the retaining structure can be omitted altogether. The retaining legs 106 are optional.

Body 102 includes first end 108 and second end 110 opposite the first end 108. Second end 110 is proximate to the retaining legs 102. Body 104 further includes inner wall 107 extending between the first end 108 and the second end 110. Inner wall 107 defines and surrounds hollow passage 104 which can be configured to conduct sound waves. Body 102 also includes outer wall 112 connected to the inner wall 107 at the first end 108. Outer wall 112 tapers away from the inner wall 107 toward the second end 110. In example aspects, outer wall 112 is frustoconical in shape. As shown in FIGS. 1-2, outer wall 112 tapers toward the second end 110 but does not necessarily reach the second end 110. In alternate embodiments not shown, outer wall 112 could extend to the second end 110 or beyond second end 110. Body 102 can be made of any suitable soft, flexible materials, including, for example, silicone, polyurethane, polynorbornene (e.g., Norsorex® material available from D-NOV GmbH of Vienna, Austria), thermoplastic elastomer (TPE), and/or fluoroelastomer.

Earpiece 100 includes electrically conductive elements 120, 122, and 124, which function as electrodes when positioned to contact skin within the ear, which generally is a stable environment offering good electrical and/or mechanical contact between skin and electrodes. Although FIG. 1 shows one particular configuration of an ear tip with electrically conductive elements 120 and 122 arranged on opposite sides of an outer surface of outer wall 112 (configured to fit at least partially into a person's ear canal), and electrically conductive element 124 arranged on body 102, this disclosure is not limited to such a configuration, and any number of electrically conductive elements can be placed in any configuration on earpiece 100 as long as the electrically conductive elements are arranged to contact skin within the ear when the earpiece is worn by a user. It should be appreciated that only two electrically conductive elements may be used to function as electrodes.

Examples of electrically conductive elements include a metal pad, metal button, metal foils (e.g., gold, silver), metal-salt hybrids (e.g., silver/silver-chloride), polymeric composites (e.g., rubbers compounded with conductive fillers such as carbon black, carbon nanotubes, graphene, silver, glass-coated silver), intrinsically conductive polymers (e.g., poly(3,4-ethylenedioxythiophene) polystyrene sulfonate or PEDOT:PSS), and/or conductive fabric (e.g., fabrics with conductive yarns, fabrics coated with conductive materials). Preferably, the electrically conductive elements are made of soft, flexible materials. The electrically conductive elements can be incorporated on to the ear tip using an ink and applying it using screen printing, pad printing, or in-mold decorating. Alternatively, the conductive elements can be incorporated wholly on to the ear tip via injection, transfer or compression molding.

Electrically conductive elements 120, 122, and/or 124 can function as physiological electrodes for detecting bioelectrical signals of an individual, including, for example, electroencephalogram (EEG), electrooculogram (EOG), electrocardiography (ECG), and electromyogram (EMG) signals, and may also be used to detect pulse rate, respiration rate, body temperature, sweat levels, and glucose, among other health parameters. Monitoring of EEG in a wearable in-ear earpiece can be used, for example, for sleep staging, stress detection, and/or music-to-mood correlation. Monitoring of EOG in a wearable in-ear earpiece can be used, for example, for sensing movement of an individual's eyes. Electrically conductive elements 120, 122, and/or 124 can also be used to deliver an electrical signal to the ear, for example, for use in nerve stimulation.

Earpiece 100 may include an embedded integrated circuit, for example, inside the body 102. In examples, earpiece 100 is communicably coupled with an integrated circuit that is separate and remotely located, for example, in a computer or a mobile device. The integrated circuit can include a data processor, a memory, and a communication processor. Commands to be executed by the processor can be obtained via the communication processor. The communication processor facilitates wired or wireless communication for earpiece 100 and can be facilitated via one or more antennas, for example. The communication processor can facilitate communication with one or more networks or other devices, for example, by using wireless methods that are known, including but not limited to Wi-Fi, Bluetooth, 3G, 4G, LTE, and/or ZigBee, among others. Earpiece 100 can further include an embedded power source (e.g., a battery) required to carry out various functionalities involving the integrated circuit and the one or more electronic components described herein.

Various example configurations of earpieces having electrically conducting elements capable of capturing bioelectrical signals and/or providing nerve stimulation are shown in FIGS. 3 through 6.

Figure 3:
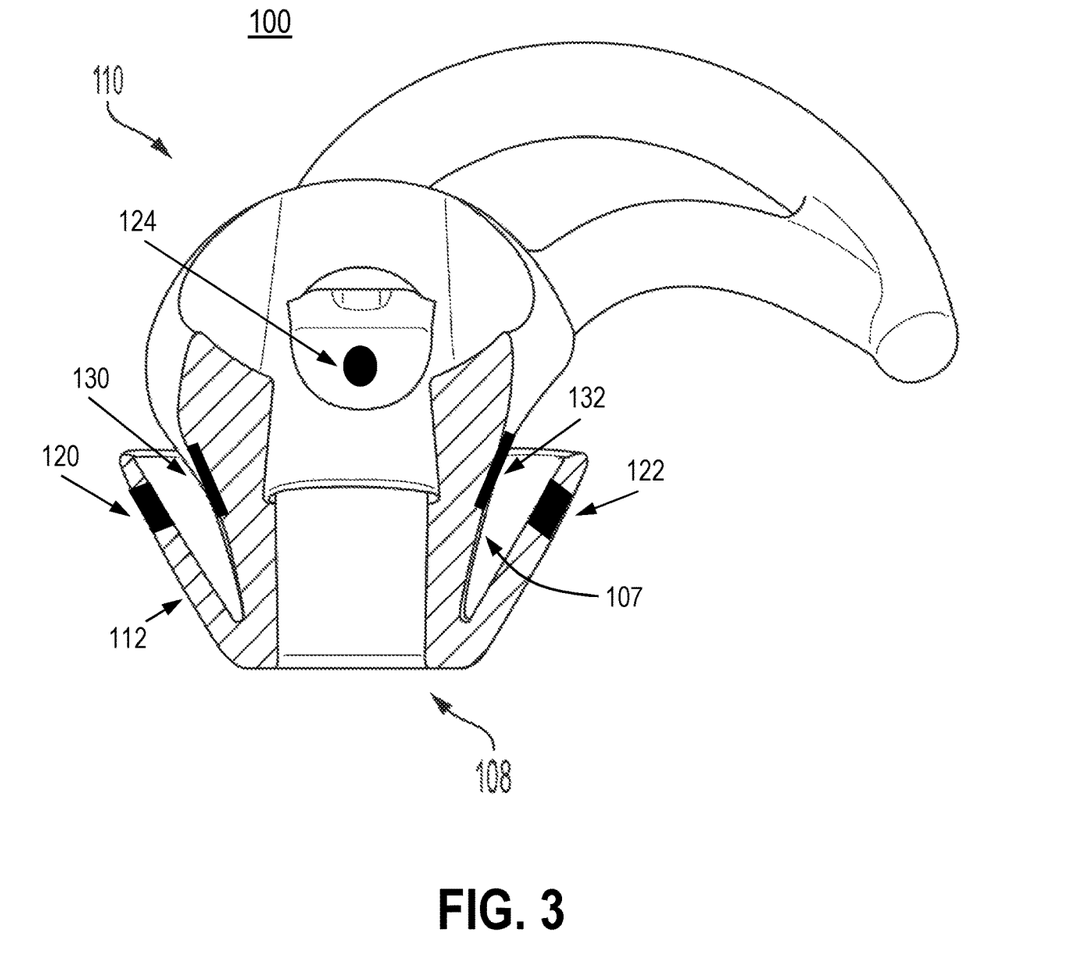
FIG. 3 illustrates an example configuration of the earpiece shown in FIG. 2, shown in a cross-sectional view generally along line 5-5 in FIG. 2.

FIG. 3 illustrates a configuration of earpiece 100 having first and second electrically conductive elements 120 and 122 arranged on an outer surface of deformable outer wall 112. Conductive elements 120 and 122 can be created, for example, by punching holes in the deformable outer wall 112 and filing the holes with silver/silver-chloride (Ag/AgCl). In FIG. 3, inner wall 107 includes first and second conductive leads 130 and 132 (e.g., metal-plated pads, such as gold-plated discs) that are configured to electrically connect with first and second electrically conductive elements 120 and 122 when outer wall 112 is deformed toward inner wall 107 as earpiece 100 is placed in the ear of an individual. The collapsing of outer wall 112 (shown in FIG. 3 in the shape of an umbrella, or frustoconical) allows for contact of electrically conductive elements 120 and 122 with respective conductive leads 130 and 132 situated behind outer wall 112, thereby establishing and transmitting electrical signals to electronics (not shown) in body 102 of the earpiece 100.

Figure 4:
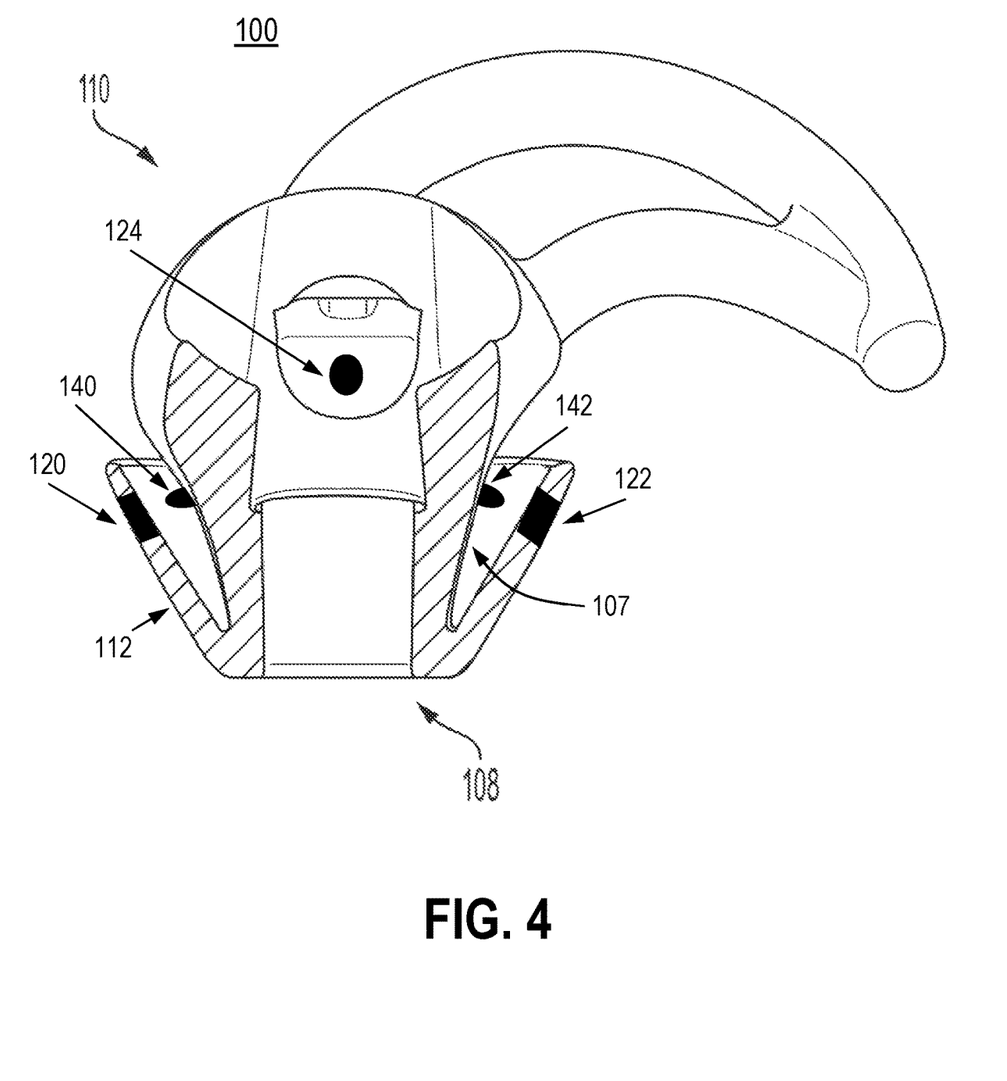
FIG. 4 illustrates an example configuration of the earpiece shown in FIG. 2, shown in a cross-sectional view generally along line 5-5 in FIG. 2.

FIG. 4 illustrates another configuration of earpiece 100 having first and second electrically conductive elements 120 and 122 arranged on an outer surface of deformable outer wall 112. In FIG. 4, inner wall 107 includes first and second conductive pins 140 and 142 (e.g., pogo pins or spring loaded connectors) that are configured to electrically connect with first and second electrically conductive elements 120 and 122 when outer wall 112 is deformed toward inner wall 107 as earpiece 100 is placed in the ear of an individual. The collapsing of outer wall 112 (shown in FIG. 4 in the shape of an umbrella, or frustoconical) allows for contact of electrically conductive elements 120 and 122 with respective conductive pins 140 and 142 situated behind deformable outer wall 112, thereby establishing and transmitting electrical signals to electronics (not shown) in body 102 of the earpiece 100. Optionally, angled through-holes may be created in the deformable outer wall 112 such that the conductive pins 140 and 142 align with the through-holes when the outer wall 112 is collapsed when placed in the ear.

Figure 5:
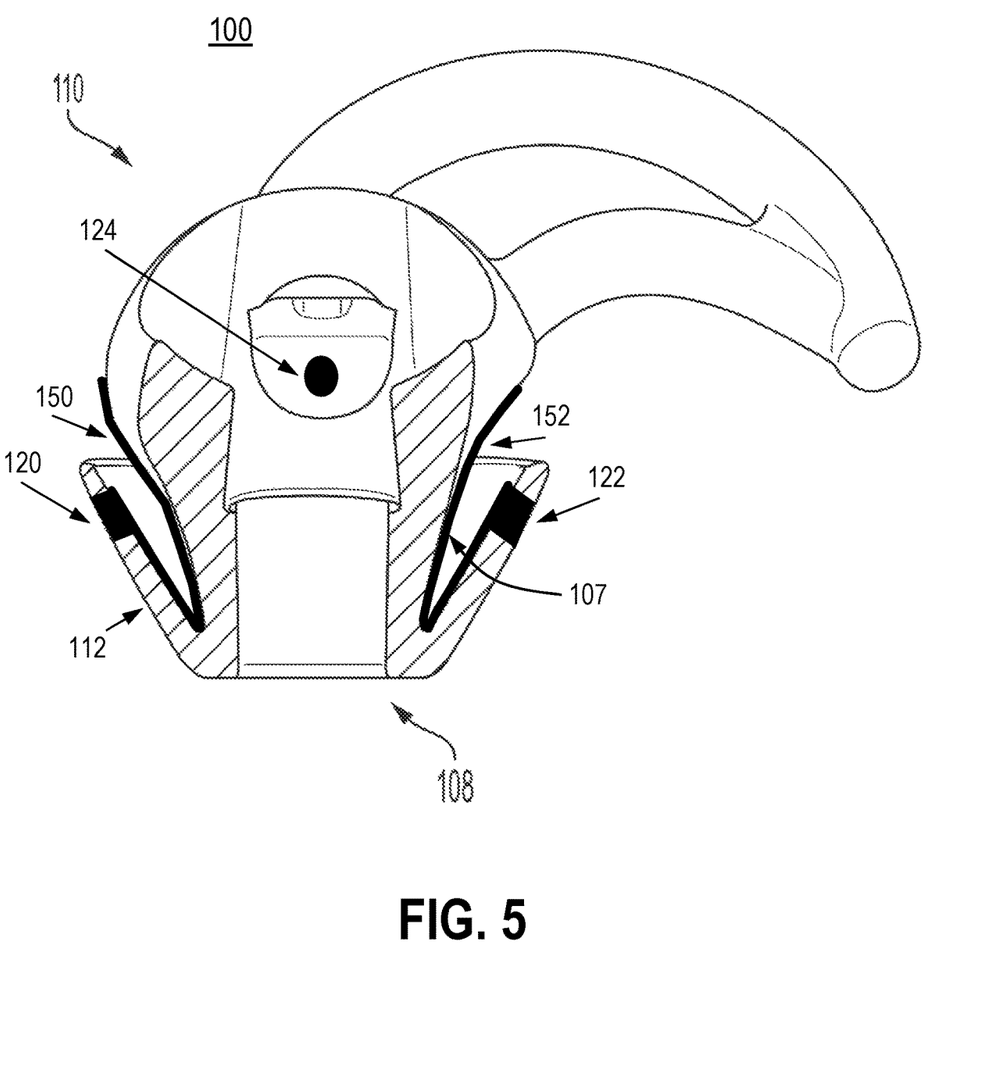
FIG. 5 illustrates an example configuration of the earpiece shown in FIG. 2, shown in a cross-sectional view generally along line 5-5 in FIG. 2.

FIG. 5 illustrates a further configuration of earpiece 100 having first and second electrically conductive elements 120 and 122 arranged on an outer surface of deformable outer wall 112. In FIG. 5, earpiece 100 includes first and second electrical circuit elements 150 and 152 (e.g., conductive fabric, such as fabric available from Eschler Textil GmbH and coated with silver/silver-chloride) connected to first and second electrically conductive elements 120 and 122. The first and second electrical circuit elements 150 and 152 each extend along an inner surface of deformable outer wall 112 and an outer surface of inner wall 107. The electrical circuit elements are connected to electronics (not shown) in body 102 of the earpiece 100, thereby allowing transmission of electrical signals when earpiece 100 is placed in the ear of an individual.

Figure 6:
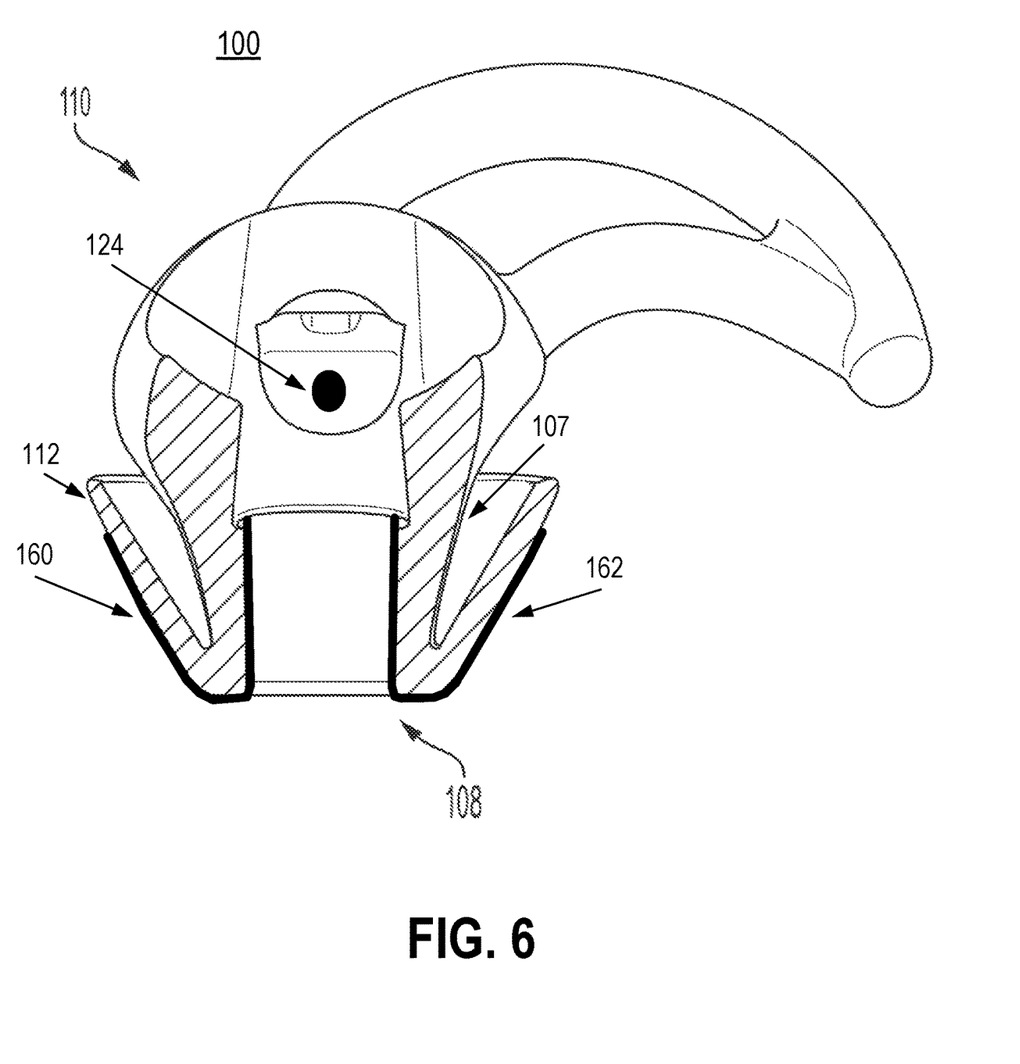
FIG. 6 illustrates an example configuration of the earpiece shown in FIG. 2, shown in a cross-sectional view generally along line 5-5 in FIG. 2.

FIG. 6 illustrates a configuration of earpiece 100 having first and second electrically conductive elements 160 and 162 (e.g., conductive fabric, such as fabric available from Eschler Textil GmbH and coated with silver/silver-chloride) each extending along an outer surface of deformable outer wall 112 and an inner surface of inner wall 107. The electrical circuit elements are connected to electronics (not shown) in body 102 of the earpiece 100, thereby allowing transmission of electrical signals when earpiece 100 is placed in the ear of an individual.

Figure 7:
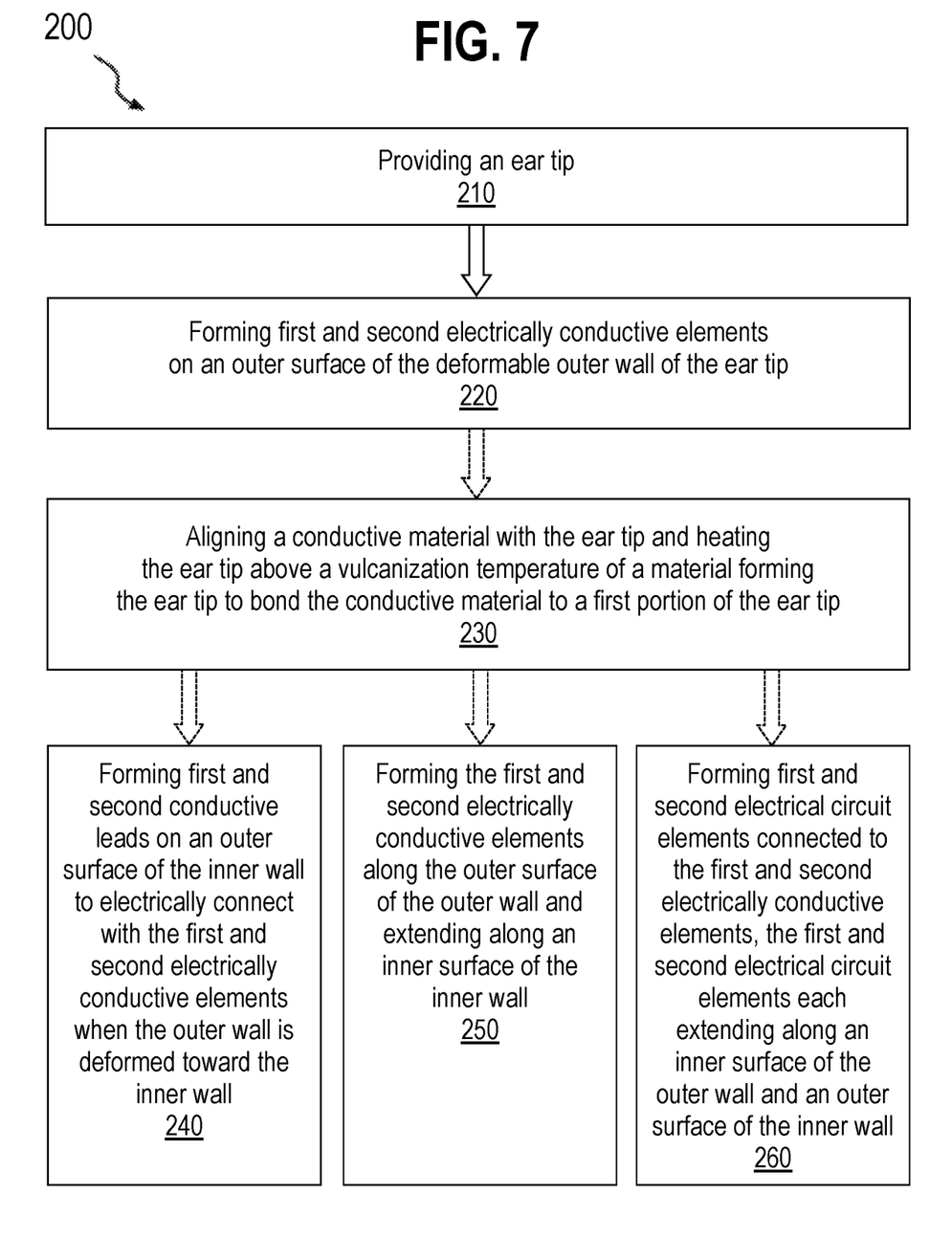
FIG. 7 is a flowchart of an example method of fabricating an ear tip configured to detect one or more bioelectrical signals and/or provide nerve stimulation.

FIG. 7 is a flowchart of an example method of fabricating an ear tip (e.g., earpiece 100) having two or more electrically conductive elements (e.g., electrically conductive elements 120 and/or 122). In step 210, an ear tip is provided. For example, the ear tip may include a body 102 having first and second ends 108 and 110, an inner wall 107 extending between the first and second ends 108 and 110 to define a hollow passage 104 to conduct acoustic energy, and a deformable outer wall 112 connected to the inner wall 107 of the body 102 at the first end 108 and tapering away from the inner wall 107 toward the second end 110, as illustrated for example in FIG. 1 of the present disclosure.

In step 220, first and second electrically conductive elements are formed on an outer surface of the deformable outer wall of the ear tip. Examples of electrically conductive elements include a metal pad, metal button, metal foils (e.g., gold, silver), metal-salt hybrids (e.g., silver/silver-chloride), polymeric composites (e.g., rubbers compounded with conductive fillers such as carbon black, carbon nanotubes, graphene, silver, glass-coated silver), intrinsically conductive polymers (e.g., poly(3,4-ethylenedioxythiophene) polystyrene sulfonate or PEDOT:PSS), and/or conductive fabric (e.g., fabrics with conductive yarns, fabrics coated with conductive materials). The electrically conductive elements are preferably made of soft, flexible materials. The electrically conductive elements can be incorporated on to the ear tip using an ink and applying it using screen printing, pad printing, or in-mold decorating. Alternatively, the conductive elements can be incorporated wholly on to the ear tip via injection, transfer or compression molding. It should be appreciated that any number of electrically conductive elements (e.g., two or more) can be placed in any configuration on an earpiece as long as the electrically conductive elements are arranged to contact skin within the ear when the earpiece is worn by a user.

Optionally, in step 230, conductive material in the first and second electrically conductive elements is aligned with the ear tip and the ear tip is heated above a vulcanization temperature of a material, causing the conductive material to bond to a first portion of the ear tip.

The electrically conductive elements can also be incorporated on to the ear tip using an ink and applying it using screen printing, pad printing, or in-mold decorating. Further, the conductive elements can be incorporated wholly on to the ear tip via injection, transfer or compression molding.

To complete the electronic circuit and allow capability of transmission of bioelectric signals and/or nerve stimulation, the conductive elements may be connected to electronics (e.g., integrated circuit, power source, etc.) in the body of the earpiece.

In one option, in step 240, first and second conductive leads (e.g., spring pins or metal-plated pads) are formed on an outer surface of the inner wall to electrically connect with the first and second electrically conductive elements when the outer wall is deformed toward the inner wall, as illustrated for example in FIGS. 3 and 4 of the present disclosure.

In another option, in step 250, first and second electrically conductive elements are formed along the outer surface of the outer wall and extending along an inner surface of the inner wall (e.g., using conductive fabrics, such as fabric available from Eschler Textil GmbH and coated with silver/silver-chloride), as illustrated for example in FIG. 5 of the present disclosure.

In a further option, in step 260, first and second electrical circuit elements are formed and connected to the first and second electrically conductive elements, with the first and second electrical circuit elements each extending along an inner surface of the outer wall and an outer surface of the inner wall (e.g., using conductive fabrics, such as fabric available from Eschler Textil GmbH and coated with silver/ silver-chloride), as illustrated for example in FIG. 6 of the present disclosure.

The various configurations of ear tips described in the present disclosure may eliminate or reduce the need for hardwiring of electrodes in earpieces and provide a more effective approach for handling the electrode lead-out. Additionally, the various configurations of ear tips described in the present disclosure allow for in-ear EEG measurement and may also enable additional features for earpieces and headsets, such as donning and doffing detection. Further, the various configurations of ear tips described in the present disclosure may be used to deliver an electrical signal to the ear, for example, for nerve stimulation.

While several inventive examples have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the inventive examples described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the inventive teachings is/are used. Those skilled in the art will recognize, or be able to ascertain using no more than routine experimentation, many equivalents to the specific inventive examples described herein. It is, therefore, to be understood that the foregoing examples are presented by way of example only and that, within the scope of the appended claims and equivalents thereto, inventive examples may be practiced otherwise than as specifically described and claimed. Inventive examples of the present disclosure are directed to each individual feature, system, article, material, and/or method described herein. In addition, any combination of two or more such features, systems, articles, materials, and/or methods, if such features, systems, articles, materials, and/or methods are not mutually inconsistent, is included within the inventive scope of the present disclosure.

Other implementations are within the scope of the following claims and other claims to which the applicant may be entitled.

What is claimed is:

1. An ear tip for an earpiece, comprising:
   a body having first and second ends, an inner wall extending between the first and second ends to define a hollow passage to conduct acoustic energy, and a deformable outer wall connected to the inner wall of the body at the first end and tapering away from the inner wall toward the second end;
   first and second electrically conductive elements arranged on an outer surface of the deformable outer wall; and
   wherein the inner wall further comprises first and second conductive leads configured to electrically connect with the first and second electrically conductive elements when the outer wall is deformed toward the inner wall.

2. The ear tip of claim 1, wherein the deformable outer wall forms a generally frustoconical shape around the inner wall.

3. The ear tip of claim 1, wherein the body is comprised of silicone, polyurethane, polynorbornene, thermoplastic elastomer (TPE), and/or fluoroelastomer.

4. The ear tip of claim 1, wherein the first and second electrically conductive elements are comprised of a metal pad, metal button, metal foil, metal-salt hybrid, polymeric composite, intrinsically conductive polymer (ICP), and/or conductive fabric.

5. The ear tip of claim 1, wherein the first and second conductive leads are comprised of spring pins or metal-plated pads.

6. An ear tip for an earpiece, comprising:
   a body having first and second ends, an inner wall extending between the first and second ends to define a hollow passage to conduct acoustic energy, and a deformable outer wall connected to the inner wall of the body at the first end and tapering away from the inner wall toward the second end;
   a first electrically conductive element arranged on an outer surface of the deformable outer wall; and
   a first conductive lead comprised in the inner wall configured to electrically connect with the first electrically conductive element when the outer wall is deformed toward the inner wall.

7. The ear tip of claim 6, wherein the deformable outer wall forms a generally frustoconical shape around the inner wall.

8. The ear tip of claim 6, wherein the body is comprised of silicone, polyurethane, polynorbornene, thermoplastic elastomer (TPE), and/or fluoroelastomer.

9. The ear tip of claim 6, wherein the first electrically conductive element is comprised of a metal pad, metal button, metal foil, metal-salt hybrid, polymeric composite, intrinsically conductive polymer (ICP), and/or conductive fabric.

10. The ear tip of claim 6, wherein the first conductive lead is comprised of at least one spring pin or metal-plated pad.

11. The ear tip of claim 6, further comprising a second electrically conductive element arranged in the body proximate to a retaining structure of the ear tip.

12. A method of fabricating an ear tip, comprising the steps of:
   providing an ear tip, wherein the ear tip comprises a body having first and second ends, an inner wall extending between the first and second ends to define a hollow passage, and a deformable outer wall connected to the inner wall of the body at the first end and tapering away from the inner wall toward the second end;
   forming first and second electrically conductive elements on an outer surface of the deformable outer wall; and
   forming first and second conductive leads on an outer surface of the inner wall to electrically connect with the first and second electrically conductive elements when the outer wall is deformed toward the inner wall.

13. The method of claim 12, wherein forming the first and second electrically conductive elements comprises: aligning a conductive material with the ear tip; and heating the ear tip above a vulcanization temperature of a material forming the ear tip to bond the conductive material to a first portion of the ear tip.

* * * * *